(12) United States Patent (10) Patent No.: US 6,974,840 B1
Luscombe et al. (45) Date of Patent: Dec. 13, 2005

(54) THERAPEUTIC AGENTS

(75) Inventors: Graham Paul Luscombe, Nottingham (GB); Patricia Lesley Needham, Nottingham (GB)

(73) Assignee: Knoll GmbH (DE)

( * ) Notice: Subject to any disclaimer, the term of this patent is extended or adjusted under 35 U.S.C. 154(b) by 0 days.

(21) Appl. No.: 10/019,802

(22) PCT Filed: Jun. 21, 2000

(86) PCT No.: PCT/EP00/05736

§ 371 (c)(1),
(2), (4) Date: May 6, 2002

(87) PCT Pub. No.: WO01/01979

PCT Pub. Date: Jan. 11, 2001

(30) Foreign Application Priority Data

Jul. 5, 1999 (GB) .............................. 9915617

(51) Int. Cl.$^7$ ............................................ A61K 31/145
(52) U.S. Cl. ...................................... 514/650; 564/339
(58) Field of Search ........................... 514/650; 564/339

(56) References Cited

U.S. PATENT DOCUMENTS 5,047,432 A    9/1991   Housley et al.

FOREIGN PATENT DOCUMENTS

| EP | 0 111 994 B1 | 9/1983 | ......... C07C/87/455 |
| EP | 0 282 206 B1 | 11/1990 | ......... A61K/31/135 |
| GB | 2 098 602 A | 4/1981 | ............ C07C/87/34 |
| WO | 94/26704 | * 11/1994 | ......... C07C/323/25 |
| WO | WO 95/2327 | * 10/1995 | ......... C07C/217/52 |
| WO | WO 98/29411 | * 7/1998 | ......... C07D/405/06 |

OTHER PUBLICATIONS

Database CAPLUS on STN, Acc. No. 1995:380315, Harris et al., WO 9426704 (abstract).*

* cited by examiner

*Primary Examiner*—Brian Davis
(74) *Attorney, Agent, or Firm*—Bromberg & Sunstein LLP

(57) ABSTRACT

Compounds of formula (I) and pharmaceutically acceptable salts thereof in which m is 0, 1 or 2; n is 2, 3, 4 or 5; X is carbonyl or a group of formula (II) in which $R_5$ is H or alkyl; Y is an alkylene chain optionally substituted by one or more alkyl groups; Z is an alkylene chain containing 2 to 5 carbon atoms optionally substituted by one or more alkyl groups; R is phenyl optionally substituted by one or more halo substituents or R is naphthyl; and $R_1$ and $R_2$, which are the same or different, are H, alkyl, or arylalkyl, provided that when $R_1$ is benzyl, $R_2$ is H or methyl; have utility in the treatment of drug misuse or other addictive disorders.

56 Claims, No Drawings

THERAPEUTIC AGENTS

This application is a 371 of PCT/EP00/05736 filed Jun. 21, 2000.

The present invention relates to compounds which are useful in the treatment of drug misuse or other addictive disorders.

WO94/26704 discloses compounds of formula I as given below as novel therapeutic agents, to processes for their preparation, to pharmaceutical compositions containing them and to their use in the treatment of depression, anxiety, Parkinson's disease, obesity, cognitive disorders, seizures, neurological disorders such as epilepsy, and as neuroprotective agents to protect against conditions such as stroke. The compounds and the pharmaceutical formulations used in the present invention may be prepared as described in WO94/26704.

The present invention provides compounds of formula I

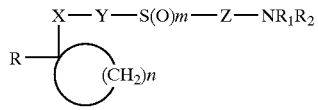

and pharmaceutically acceptable salt's thereof in which
m is 0, or 2;
n is 2, 3, 4 or 5;
X is carbonyl or a group of formula II

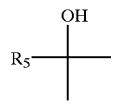

in which $R_5$ is H or an alkyl group containing 1 to 4 carbon atoms;
Y is an alkylene chain containing 1 or 2 carbon atoms optionally substituted by one or more alkyl groups containing 1 to 3 carbon atoms;
Z is an alkylene chain containing 2 to 5 carbon atoms optionally substituted by one or more alkyl groups containing 1 to 3 carbon atoms;
R is phenyl optionally substituted by one or more halo substituents which are the same or different (for example fluoro, chloro, bromo or iodo) or R is naphthyl; and
$R_1$ and $R_2$, which are the same or different, are H, a straight or branched chain alkyl group containing 1 to 4 carbon atoms, an arylalkyl group in which the alkyl group contains 1 to 3 carbon atoms, provided that when $R_1$ is benzyl, $R_2$ is H or methyl; for use in the treatment of drug misuse or other addictive disorders.

In preferred compounds of formula I, m is 0, 1 or 2 and n is 3 or 4.

In preferred compounds of formula I, X is carbonyl or a group of formula II in which $R_5$ is H.

In preferred compounds of formula I, Y is methylene.

In preferred compounds of formula I, Z is an alkylene chain containing 2, 3 or 4 carbon atoms optionally substituted by one or more alkyl groups containing 1 to 3 carbon atoms. In more preferred compounds of formula I, Z is an alkylene chain containing 2, 3 or 4 carbon atoms optionally substituted by one or more methyl groups.

In preferred compounds of formula I, R is phenyl substituted by one or two chloro substituents, or R is naphthyl. In more preferred compounds of formula I, R is 3-chlorophenyl, 3,4-dichlorophenyl or 2-naphthyl.

In preferred compounds of formula I, $R_1$ is an alkyl group containing 1 to 3 carbon atoms or is benzyl, and $R_2$ is an alkyl group containing 1 to 3 carbon atoms. In more preferred compounds of formula I, $R_1$ and $R_2$ are both methyl or ethyl or $R_1$ is benzyl and $R_2$ is methyl. In especially preferred compounds of formula I, $R_1$ and $R_2$ are both methyl.

A preferred group of compounds of formula I is represented by formula III

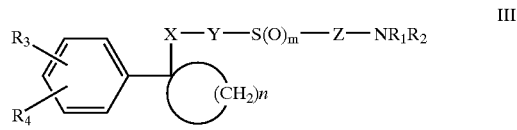

and pharmaceutically acceptable salts thereof in which m, n, X, Y, Z, $R_1$ and $R_2$ are as described above for formula I; and $R_3$ is halo (for example fluoro, chloro, bromo or iodo), and $R_4$ is H or halo (for example fluoro, chloro, bromo or iodo), or $R_3$ and $R_4$ together with the carbon atoms to which they are attached form a fused benzene ring.

In more preferred compounds of formula III, $R_3$ is chloro and $R_4$ is H, $R_3$ and $R_4$ are both chloro or $R_3$ and $R_4$ together with the carbon atoms to which they are attached form a fused benzene ring. In especially preferred compounds of formula III, $R_3$ is chloro situated in the 3-substitution position on the phenyl ring and $R_4$ is H, $R_3$ and $R_4$ are both chloro and are situated in the 3- and 4-substitution positions on the phenyl ring respectively, or $R_3$ and $R_4$ together with the phenyl ring to which they are attached form a 2-naphthyl group.

Compounds of formula I and III may exist as salts with pharmaceutically acceptable acids. Examples of such salts include hydrochlorides, hydrobromides, sulphates, methanesulphonates, nitrates, maleates, acetates, citrates, fumarates, tartrates [eg (+)-tartrates, (−)-tartrates or mixtures thereof including racemic mixtures], succinates, benzoates and salts with amino acids such as glutamic acid. Compounds of formula I and III and their salts may exist in the form of solvates (for example hydrates).

Certain compounds of formula I and III may exist in more than one crystal form and the present invention includes each crystal form and mixtures thereof.

It will be appreciated by those skilled in the art that compounds of formula I and III may contain one or more chiral centres. When compounds of formula I and III contain one chiral centre, the compounds exist in two enantiomeric forms and the present invention includes both enantiomers and mixtures of those enantiomers. The individual enantiomers may be obtained by methods known to those skilled in the art. Such methods typically include resolution via formation of diastereoisomeric salts which may be separated, for example, by crystallisation; via formation of diastereoisomeric derivatives or complexes which may be separated, for example, by crystallisation, gas-liquid or liquid chromatography; via selective reaction of one enantiomer with an enantiomer-specific reagent, for example enzymatic esterification, oxidation or reduction; or via gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesised by asymmetric synthesis using optically active reagents, substrates, catalysts or solvents, or by converting one enantiomer into the other by asymmetric transformation.

When compounds of formula I and III contain more than one chiral centre, the compounds may exist in diastereoisomeric forms. The diastereoisomeric pairs may be separated by methods known to those skilled in the art, for example chromatography or crystallisation and the individual enantiomers within each pair may be separated as described above. The present invention includes each diastereoisomer of compounds of formula I and III and mixtures thereof.

Specific compounds of formula I and III are:

1-[1-(3,4-dichlorophenyl)cyclobutyl]-2-[2-dimethylamino)ethylthio]ethanone;

1-[1-(3,4-dichlorophenyl)cyclobutyl]-2-[2-(dimethylamino)ethylsulphinyl]ethanone;

1-[1-(3,4-dichlorophenyl)cyclobutyl]-2-[2-(dimethylamino)ethylsulphonyl]ethanone;

1-[1-(3,4-dichlorophenyl)cyclobutyl]-2-[2-diethylamino)ethylthio]ethanone;

2-[2-(N-benzyl-N-methylamino)ethylthio]-1-[1-(3,4-dichlorophenyl)cyclobutyl]ethanone;

1-[1-(3,4-dichlorophenyl)cyclobutyl]-2-[2-(dimethylamino)ethylthio]ethanol;

1-[1-(3,4-dichlorophenyl)cyclobutyl]-2-[3-(dimethylamino)propylthio]ethanone;

1-[1-(3,4-dichlorophenyl)cyclobutyl]-2-[3-(dimethylamino)propylsulphonyl]ethanone;

1-[1-(3,4-dichlorophenyl)cyclobutyl]-2-[3-(dimethylamino)propylthio]ethanol;

1-[1-(3,4-dichlorophenyl)cyclobutyl]-2-[3-(dimethylamino)-2-methylpropylthio]ethanone;

2-[2-(dimethylamino)ethylthio]-1-[1-(2-naphthyl)cyclobutyl]ethanone;

1-[1-(3-chlorophenyl)cyclobutyl]-2-[3-(dimethylamino)propylthio]ethanone;

1-[1-(3,4-dichlorophenyl)cyclobutyl]-2-[4-(dimethylamino)butylthio]ethanone;

1-[1-(3,4-dichlorophenyl)cyclobutyl]-2-[3-(dimethylamino)propylthio]ethanone;

and pharmaceutically acceptable salts thereof in the form of individual enantiomers, racemates, or other mixtures of enantiomers.

Specific enantiomerc forms of compounds of formula I and III are:

(−)-1-[1-(3,4-dichlorophenyl)cyclobutyl]-2-[3-(dimethylamino)propylthio]ethanol;

(+)-1-[1-(3,4-dichlorophenyl)cyclobutyl]-2-[3-(dimethylamino)propylthio]ethanol;

The present invention also includes pharmaceutical compositions containing a therapeutically effective amount of a compound of formula I or III together with a pharmaceutically acceptable diluent or carrier.

As used hereinafter, the term "active compound" denotes a compound of formula I or III. In therapeutic use, the active compound may be administered orally, rectally, parenterally or topically, preferably orally. Thus the therapeutic compositions of the present invention may take the form of any of the known pharmaceutical compositions for oral, rectal, parenteral or topical administration. Pharmaceutically acceptable carriers suitable for use in such compositions are well known in the art of pharmacy. The compositions of the invention may contain 0.1–99% by weight of active compound. The compositions of the invention are generally prepared in unit dosage form.

Compositions for oral administration are the preferred compositions of the invention and these are the known pharmaceutical forms for such administration, for example tablets, capsules, granules, syrups, solutions and aqueous or oil suspensions. The excipients used in the preparation of these compositions are the excipients known in the pharmacist's art. Tablets may be prepared by mixing the active compound with fillers, for example calcium phosphate; disintegrating agents, for example maize starch; lubricating agents, for example magnesium stearate; binders, for example micro-crystalline cellulose or polyvinylpyrrolidone and other optional ingredients known in the art to permit tableting the mixture by known methods. The tablets may, if desired, be coated using known methods and excipients which may include enteric coating using for example hydroxypropylmethyl cellulose phthalate. The tablets may be formulated in a manner known to those skilled in the art so as to give a sustained release of the compounds of the present invention. Such tablets may, if desired, be provided with enteric coatings by known methods, for example by the use of cellulose acetate phthalate. Similarly, capsules, for example hard or soft gelatin capsules, containing the active compound with or without added excipients, may be prepared by conventional means and, if desired, provided with enteric coatings in a known manner. The contents of the capsule may be formulated using known methods so as to give sustained release of the active compound. The tablets and capsules may conveniently each contain 1 to 500 mg of the active compound.

Other compositions for oral administration include, for example, aqueous suspensions containing the active compound in an aqueous medium in the presence of a non-toxic suspending agent such as sodium carboxymethyl-cellulose, and oily suspensions containing a compound of the present invention in a suitable vegetable oil, for example arachis oil. The active compound may be formulated into granules with or without additional excipients. The granules may be ingested directly by the patient or they may be added to a suitable liquid carrier (for example, water) before ingestion. The granules may contain disintegrants, for example an effervescent couple formed from an acid and a carbonate or bicarbonate salt to facilitate dispersion in the liquid medium.

Compositions of the invention suitable for rectal administration are the known pharmaceutical forms for such administration, for example, suppositories with cocoa butter or polyethylene glycol bases.

Compositions of the invention suitable for parenteral administration are the known pharmaceutical forms for such administration, for example sterile suspensions or sterile solutions in a suitable solvent.

Compositions for topical administration may comprise a matrix in which the pharmacologically active compounds of the present invention are dispersed so that the compounds are held in contact with the skin in order to administer the in compounds transdermally. Alternatively the active compounds may be dispersed in a pharmaceutically acceptable cream, gel or ointment base. The amount of active compound contained in a topical formulation should be such that a therapeutically effective amount of the compound is delivered during the period of time for which the topical formulation is intended to be on the skin.

The compounds of the present invention may also be administered by continuous infusion either from an external source, for example by intravenous infusion or from a source of the compound placed within the body. Internal sources include implanted reservoirs containing the compound to be infused which is continuously released for example by osmosis and implants which may be (a) liquid such as a suspension or solution in a pharmaceutically acceptable oil of the compound to be infused for example in the form of a very sparingly water-soluble derivative such as a dodecanoate salt of a compound of formula I or III or (b)solid in the form of an implanted support, for example of a synthetic resin or waxy material, for the compound to be infused. The support may be a single body containingall the compound or a series of several bodies each containing part of the compound to be delivered. The amount of active compound present in an internal source should be such that a therapeutically effective amount of the compound is delivered over a long period of time.

In some formulations it may be beneficial to use the compounds of the present invention in the form of particles of very small size, for example as obtained by fluid energy milling.

In the compositions of the present invention the active compound may, if desired, be associated with other compatible pharmacologically active ingredients.

The pharmaceutical compositions containing a therapeutically effective amount of a compound of formula I or III may be used to treat drug misuse or other addictive disorders. Whilst the precise amount of active compound administered in such treatment will depend on a number of factors, for example the age of the patient, the severity of the condition and the past medical history, and always lies within the sound discretion of the administering physician, the amount of active compound administered per day is in the range 1 to 1000 mg preferably 5 to 500 mg given in single or divided doses at one or more times during the day.

In another aspect the present invention provides a method of treating drug misuse or other addictive disorders which comprises the administration of a therapeutically effective amount of a compound of formula I to a patient in need thereof.

The present invention provides a method of reducing cravings to food or an addictive substance in a mammal comprising administering an effective amount of a compound of formula I to a mammal in need thereof.

Suitably the addictive substance is cocaine, amphetamine, nicotine, opiates, tobacco or alcohol. The addictive substance may also be MDMA (ecstasy), a cannabinoid, LSD, MDA or PCP. The term opiates includes heroin and morphine.

In yet another aspect, the present invention provides the use of a compound of formula I or III in the manufacture of a medicament for use in the treatmentof drug misuse or other addictive disorders.

Conditions which may be advantageously treated with the compounds of the present invention include disorders arising from drug misuse including drug withdrawal symptoms, aiding in the cessation of smoking, aiding in the prevention of relapse after cessation of drug use and similar use in the treatment of other addictive disorders such as compulsive gambling, compulsive shopping disorder and compulsive sexual disorder.

In another aspect the present invention provides a method of treating addictive-drug-induced psychoses comprising administering a therapeutically effective amount of a compound of formula I to a mammal, particularly a human being, in need thereof. The addictive drug is selected from one or more of the following: a benzodiazepine; a cannabinoid, LSD, MDMA, MDA, PCP, an opiate including heroin and morphine, amphetamine, cocaine and alcohol.

The pharmacological activity of the compounds of the present invention may be demonstrated by one or more of the following tests.

Study 1 Methods

Subjects: The subjects are four male rhesus monkeys (*Macaca mulatta*), weighing 5.7–8.1 kg and maintained on a diet of 3–4 monkey biscuits and one piece of fresh fruit per day. During the week, all food is delivered after the experimental session, whereas at weekends, food is delivered between 9 a.m. and noon. Water is freely available at all times. The monkeys are housed in a humidity and temperature controlled room with a 12 h lightark cycle (lights on from 7 a.m. to 7 p.m.).

Apparatus: Each monkey is housed individually in a well-ventilated, stainless steel chamber (56×71×69 cm) which includes an operant panel (28×28 cm) mounted on the front wall. Three response keys are arranged in a horizontal row 3.2 cm from the top of the operant panel. Each key can be transilluminated by red or green stimulus lights (Superbright LEDs). An externally mounted pellet dispenser delivers 1 g fruit-flavoured food pellets to a food receptacle beneath the operant response panel. A computer, located in a separate room, controls the operant panels and data collection.

Discrimination Training: Discrimination training is conducted 5 days per week during daily sessions composed of multiple cycles. Each cycle consists of a 15 min time-out period followed by a 5 min response period. During the time-out, all stimulus lights are off, and responding has no scheduled consequences. During the response period, the right and left response keys are transilluminated red or green, and monkeys can earn up to 10 food pellets by responding under a FR 30 schedule of food presentation. For one monkey, the left key is illuminated green and the right key is illuminated red, the colours of the responsekeys are reversed for the other three monkeys. The centre key is not illuminated at any time and responding on it has no scheduled consequences. If all available food pellets are delivered before the end of the 5 min response period, the stimulus lights are turned off and responding has no scheduled consequences for the remainder of the 5 min period.

On training days, monkeys are given either saline or 0.40 mg/kg cocaine, i.m., 10 min before the response period. Following the administration of saline, responding on only the green key (the saline-appropriate key) produces food, whereas following administration of 0.40 mg/kg cocaine, only responding on the red key (the drug-appropriate key) produces food. Responses on the inappropriate key reset the FR requirement on the appropriate key. Sessions consist of 1 to 5 cycles and, if cocaine is administered, this occurs only during the last cycle. Thus, training days consist of 0 to 5 saline cycles followed by 0 or 1 cocaine cycle.

During each response period, 3 dependent variables are determined:

1) Percent injection-appropriate responding prior to delivery of the first reinforcer.
2) Percent injection-appropriate responding for the entire response period
3) Response Rate.

Monkeys meeting the following criteria during the training day immediately proceeding the test day and in at least 6 of 7 consecutive training sessions before this are used for discrimination testing:

1) the percent injection-appropriate responding prior to delivery of the first reinforcer is $\geq 80\%$ for all cycles;
2) the percent injection-appropriate responding for the entire cycle is $\geq 90\%$ for all cycles;

3) Response rates during saline training cycles are >0.5 responses per second.

If responding did not meet criterion levels of discrimination performance, then, training is continued until criterion levels of performance are obtained for at least two consecutive days.

Discrimination Testing: Test sessions are identical to training sessions except that responding on either key produces food, and the test compound is administered using a Pretreatment Protocol. In this protocol, a cumulative dose-effect curve for cocaine (0.013–1.3 mg/kg) is determined either alone or following pretreatment with the test compound, which is administered 20 min before the first dose of cocaine.

Mean data from saline and drug cycles during the training day immediately proceeding the initial test day serve as the control data for the subsequent test day.

Data Analysis: The Percent Cocaine-Appropriate Responding and the Response Rate are plotted as a function of the dose of cocaine (log scale). Where possible, the $ED_{50}$ value for cocaine is determined by drawing a line between the points above and below 50% cocaine-appropriate responding, and then using linear regression to interpolate the dose that would produce 50% cocaine-appropriate responding. $ED_{50}$ values for cocaine administered alone and following pretreatment with the test compound are then compared.

Drugs: Cocaine hydrochloride is dissolved in sterile saline. The test compound is dissolved in 1% lactic add in distilled water.

Results

Control mean saline-appropriate responding=99.8% (±10.2) and 100% appropriate responding are obtained during cocaine cycles.

$ED_{50}$ values for cocaine are calculated. Administration of cocaine alone produces a dose-dependent increase in cocaine-appropriate responding in all four monkeys. Complete substitution is obtained at the training dose of cocaine (0.4 mg/kg) in all monkeys, and a higher dose of 1.3 mg/kg usually decreases response rates. Pretreatment with 0.01 mg/kg of the test compound produces a rightward shift in the cocaine dose-effect curve and a 3-fold increase in the cocaine $ED_{50}$ value in monkey 2, but it has no effect on the cocaine discrimination dose-effect curve in the other three monkeys. A higher dose of 0.032 mg/kg of the test compound produces rightward shifts in the cocaine dose-effect curves in all four monkeys. The test compound (0.01 and 0.032 mg/kg) also eliminated responding during the first one to three cycles of the cumulative cocaine dose-effect curve determination (i.e. in combination with 0.013 and 0.04 mg/kg cocaine). However, monkeys responded after administration of higher cocaine doses, thereby permitting evaluation of the effects on cocaine discrimination. Interestingly, response rates following administration of the highest dose of cocaine (1.3 mg/kg) are often higher following test compound pretreatment than for cocaine alone, suggesting that the test compound attenuated the rate-decreasing effects of high cocaine doses.

These studies can establish that the test compound antagonises the discriminative stimulus effects and possibly also the rate decreasing effects of cocaine at doses that also produce effects on response rates by comparing $ED_{50}$ values (mg/kg) for cocaine administered either alone or after pretreatment with test compound.

Study 2 Methods

Subjects: The subjects are four male rhesus monkeys (*Macaca mulatta*). Each monkey is maintained on a diet of 3 monkey biscuits and one piece of fresh fruit per day in addition to fruit-flavoured pellets delivered during operant sessions (see below). Water is freely available at all times. The monkeys are housed in a humidity and temperature controlled room with a 12 hr light-dark cycle (lights on from 7 a.m. to 7 p.m.).

Monkeys are surgically implanted with double-lumen silicone rubber catheters (inside diameter 0.7 mm, outside diameter 2.0 mm) to facilitate concurrent delivery of cocaine and treatment compounds. Catheters are implanted in the jugular or femoral vein and exteriorized in the midscapular region. All surgical procedures are performed under aseptic conditions. Monkeys are sedated with ketamine (5 mg/kg, s.c,), and anaesthesia is induced with sodium thiopental (10 mg/kg, i.v). Monkeys receive 0.05 mg/kg atropine, to reduce salivation. Following insertion of a tracheal tube, anaesthesia is maintained with isoflurane (1–1.5% in oxygen). After surgery, monkeys are administered aspirin or acetaminophen (80–160 mg/day; p.o.) for 3 days and Procaine Penicillin 0 (300,000 units/day, i.m.) every day for 5 days. The i.v. catheter is protected by a tether system consisting of a custom-fitted nylon vest connected to a flexible stainless steel cable and fluid swivel (Lomir Biomedical; Malone, N.Y.), which permits the monkeys to move freely. Catheter patency is periodically evaluated by i.v. administration of the short-acting barbiturate methohexital (3 mg/kg i.v.) or ketamine (2–3 mg/kg i.v.). The catheter is considered patent if i.v. administration of methohexital or ketamine produces loss of muscle tone within 10 seconds after its administration.

Apparatus: Each monkey is housed individually in a well-ventilated stainless steel chamber (64×64×79 cm which includes an operant panel (28×28 cm) mounted on the front wall. Three response keys (6.4×6.4 cm) are arranged in a horizontal row 3.2 cm from the top of the operant panel. Each key can be transilluminated by red or green stimulus lights (Superbright LEDs). An externally mounted pellet dispenser delivers 1 g fruit-flavoured food pellets to a food receptacle beneath the operant response panel. Two syringe pumps are mounted above each cage for delivery of saline or drug solutions through the intravenous catheters. Operant panels and data collection are controlled by a computer through a MED-PC interface.

Training: Food and i.v. drug or saline injections are available during three alternating components: a 5 min food component, a 100-min drug component, and a second 5 min food component. Both food and i.v. injections are available under a FR 30 schedule of reinforcement. During the two food components, the response key is transilluminated red. During the drug component, the response key is transilluminated green. Following the delivery of each food pellet or drug injection, there is a 10 sec time-out period, during which the stimulus light illuminating the centre response key is turned off and responding has no scheduled consequences. The food and drug components are separated by 5-min time-out periods when the response key is dark, and responding has no scheduled consequences. The entire food/drug/food session lasts 120 min.

In addition to the food/drug/food session described above, monkeys are also given the opportunity to self-administer additional food pellets during supplementary food sessions. During these sessions, food is available under a FR30/Timeout 10 sec schedule, and a maximum of 25 pellets per session can be earned. These food sessions provide additional enrichment opportunities for the monkeys and behavioural information relevant for the evaluation of prolonged treatment drug effects.

During training, the solution available for self-administration during the drug component is alternated between 0.032 mg/kg/inj cocaine (the maintenance dose of cocaine) and saline. Each period of cocaine or saline availability usually lasts from 3 to 10 days. Monkeys are trained until they met the following criteria for stable cocaine self-administration: 1) three consecutive days during which the response rate during the drug component of each session differs by no more than 20% from the mean drug component response rate and there is no upward or downward trend; and 2) rapid saline extinction as indicated by a decrease in drug component response rates on the first day of saline substitution.

Evaluation of Test Compound: The effects of the test compound (0.0032–0.10 mg/kg) on cocaine self-administration and food-maintained behaviour are evaluated using the standard pretreatment test procedure. In this procedure, the test compound is administered i.m. 20-min prior to a test session during which a test unit dose of cocaine is available during the drug component. Two series of studies are described here. In the first, the unit dose of cocaine is 0.0032 mg/kg/inj (at or near the peak of each monkey's cocaine self-administration dose-effect curve) and the effects of pretreatment with each dose of test compound are determined in single sessions for all monkeys. In the second series of studies, the effects of pretreatment with each of two doses of the test compound (0.003 and 0.01 mg/kg) on the entire cocaine dose-effect function are determined. In these studies, the dose of cocaine is systematically varied for single test sessions after pretreatment with each dose of the test compound. Both the dose of cocaine and the pretreatment dose of the test compound are varied across test sessions in an irregular order among monkeys.

At the conclusion of each pretreatment test in either series of studies, training conditions (availability of saline or the maintenance dose of cocaine) are reinstated. Test sessions generally are conducted on Tuesdays and Fridays, and either saline or the maintenance dose of cocaine is available during training sessions for the remainder of the week. On occasion, another dose of cocaine is substituted for the maintenance dose to insure that the position of the cocaine dose-effect function in individual monkeys is stable. In addition, test days are occasionally omitted to allow iseveral days of saline substitution.

Data Analysis: The dependent variables are the response rates during each food and drug component. The response rate is calculated as [total # responses (component duration—S time-outs)]. Control response rates for each food and drug component during availability of each unit dose of cocaine are defined as the response rate obtained when that unit dose of cocaine is available and no pretreatment is administered. The $ED_{50}$ value for the test compound during each food or drug component is defined as the dose of the test compound that decreases rates of cocaine or food self-administration to 50% of control response rates. The $ED_{50}$ values are determined where possible by linear regression from the linear portion of the test compound dose-effect curve.

For subsequent studies, in which the unit dose of cocaine is varied and the pretreatment dose of the test compound is held constant, response rates are graphed as a function of the unit dose of cocaine. Control cocaine dose-effect curves are determined in the absence of pretreatment and are visually compared to cocaine dose-effect curves determined following pretreatment with the test compound.

Drugs: Cocaine hydrochloride is dissolved in saline. A stock solution of 10 mg/ml of the test compound is prepared using a vehicle of 1% lactic acid in distilled water, and dilutions are made with distilled water. Aseptic precautions are taken in every phase of cocaine solution preparation and dispensing. Cocaine solutions are filter-sterilised using a 0.22 micron Millipore Filter and stored in stenile, pyrogen-free vials. Sterility of the entire fluid path for drug solutions is maintained throughout the study. Each unit dose of cocaine is delivered i.v. in an injection volume of 0.1 ml. Doses of the test compound are delivered i.m. in a volume of 0.2–3.0 ml.

These studies can establish that treatment with the test compound diminishes cocaine self-administration and food-maintained behaviour.

What is claimed is:

1. A method of treating drug misuse or other addictive disorders comprising administering a therapeutically effective amount of a compound of formula I

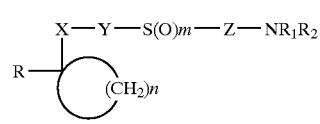

and pharmaceutically acceptable salts thereof in which
m is 0, 1 or 2;
n is 2, 3, 4 or 5;
X is carbonyl or a group of formula II

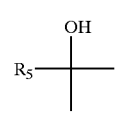

in which $R_5$ is H or an alkyl group containing 1 to 4 carbon atoms;
Y is an alkylene chain containing 1 or 2 carbon atoms optionally substituted by one or more alkyl groups containing 1 to 3 carbon atoms;
Z is an alkylene chain containing 2 to 5 carbon atoms optionally substituted by one or more alkyl groups containing 1 to 3 carbon atoms;
R is phenyl optionally substituted by one or more halo substituents or R is naphthyl; and
$R_1$ and $R_2$ which are the same or different, are H, a straight or branched chain alkyl group containing 1 to 4 carbon atoms, an arylalkyl group in which the alkyl group contains 1 to 3 carbon atoms, provided that when $R_1$ is benzyl, $R_2$ is H or methyl;
to a patient in need thereof.

2. A method according to claim 1, wherein m is 0, 1 or 2 and n is 3 or 4.

3. A method according to claim 1, wherein X is carbonyl or the group of formula II in which $R_5$ is H.

4. A method according to claim 1, wherein Y is methylene.

5. A method according to claim 1, wherein Z is an alkylene chain containing 2 to 4 carbon atoms optionally substituted by one or more alkyl groups containing 1 to 3 carbon atoms.

6. A method according to claim 1, wherein Z is an alkylene chain containing 2 to 4 carbon atoms optionally substituted by one or more methyl groups.

7. A method according to claim 1, wherein R is phenyl substituted by one or two chloro substituents or R is naphthyl.

8. A method according to claim 1, wherein R is 3-chlorophenyl; 3,4-dichlorophenyl; or 2-naphthyl.

9. A method according to claim 1, wherein $R_1$ is an alkyl group containing 1 to 3 carbon atoms or is benzyl, and $R_2$ is an alkyl group containing 1 to 3 carbon atoms.

10. A method according to claim 1, wherein $R_1$ and $R_2$ are both methyl or ethyl or $R_1$ is benzyl and $R_2$ is methyl.

11. A method of treating drug misuse or other addictive disorders comprising administering a therapeutically effective amount of a compound of formula III

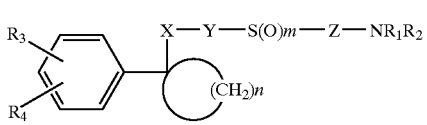

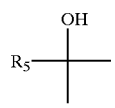

and pharmaceutically acceptable salts thereof wherein:
m is 0, 1 or 2;
n is 2, 3, 4 or 5;
X is carbonyl or a group of formula II

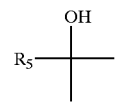

and wherein $R_5$ is H or an alkyl group containing 1 to 4 carbon atoms;
Y is an alkylene chain containing 1 or 2 carbon atoms optionally substituted by one or more alkyl groups containing 1 to 3 carbon atoms;
Z is an alkylene chain containing 2 to 5 carbon atoms optionally substituted by one or more alkyl groups containing 1 to 3 carbon atoms;
$R_1$ and $R_2$, which are the same or different, are H, a straight or branched chain alkyl group containing 1 to 4 carbon atoms, an arylalkyl group in which the alkyl group contains 1 to 3 carbon atoms, provided that when $R_1$ is benzyl, $R_2$ is H or methyl; and
$R_3$ is halo, and $R_4$ is H or halo, or $R_3$ and $R_4$ together with the carbon atoms to which they are attached form a fused benzene ring;
to a patient in need thereof.

12. A method according to claim 11, wherein $R_3$ is chloro and $R_4$ is H, $R_3$ and $R_4$ being both chloro or $R_3$ and $R_4$ together with the carbon atoms to which they are attached forming a fused benzene ring.

13. A method according to claim 11, wherein $R_3$ is chloro situated in the 3-substitution position on the phenyl ring and $R_4$ is H, $R_3$ and $R_4$ being both chloro and situated in the 3- and 4-substitution positions on the phenyl ring respectively, or $R_3$ and $R_4$ together with the phenyl ring to which they are attached forming a 2-naphthyl group.

14. A method according to claim 1, wherein the compound of formula I is selected from the group consisting of:
1-[1-(3,4-dichlorophenyl)cyclobutyl]-2-[2-(dimethylamino)ethylthio]ethanone;
1-[1-(3,4-dichlorophenyl)cyclobutyl]-2-[2-(dimethylamino)ethylsulphinyl]ethanone;
1-[1-(3,4-dichlorophenyl)cyclobutyl]-2-[2-(dimethylamino)ethylsulphonyl]ethanone;
1-[1-(3,4-dichlorophenyl)cyclobutyl]-2-[2-(diethylamino)ethylthio]ethanone;
2-[2-(N-benzyl-N-methylamino)ethylthio]-1-[1-(3,4-dichlorophenyl)cyclobutyl]ethanone;
1-[1-(3,4-dichlorophenyl)cyclobutyl]-2-[2-(dimethylamino)ethylthio]ethanol;
1-[1-(3,4-dichlorophenyl)cyclobutyl]-2-[3-(dimethylamino)propylthio]ethanone;
1-[1-(3,4-dichlorophenyl)cyclobutyl]-2-[3-(dimethylamino)propylsulphonyl]ethanone;
1-[1-(3,4-dichlorophenyl)cyclobutyl]-2-[3-(dimethylamino)propylthio]ethanol;
1-[1-(3,4-dichlorophenyl)cyclobutyl]-2-[3-(dimethylamino)-2-methylpropylthio]-ethanone;
2-[2-(dimethylamino)ethylthio]-1-(1-(2-naphthyl)cyclobutyl]ethanone;
1-[1-(3-chlorophenyl)cyclobutyl]-2-[3-(dimethylamino)propylthio]ethanone;
1-[1-(3,4-dichlorophenyl)cyclobutyl]-2-[4-(dimethylamino)butylthio]ethanone;
1-[1-(3,4-dichlorophenyl)cyclobutyl]-2-[3-(dipropylamino)propylthio]ethanone;
1-[1-(3,4-dichlorophenyl)cyclobutyl]-2-[3-(dimethylamino)-2-methylpropylthio]ethanol;
1-[1-(3,4-dichlorophenyl)cyclopentyl]-2-[3-(dimethylamino)propylthio]ethanone; and
pharmaceutically acceptable salts thereof in the form of individual enantiomers, racemates, or other mixtures of enantiomers.

15. A method of reducing cravings to an addictive substance in a mammal comprising administering an effective amount of a compound of formula I

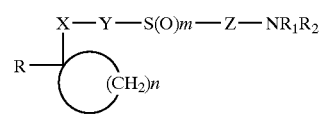

and pharmaceutically acceptable salts thereof in which
m is 0, 1 or 2;
n is 2, 3, 4 or 5;
X is carbonyl or a group of formula II

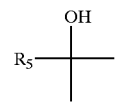

in which $R_5$ is H or an alkyl group containing 1 to 4 carbon atoms;
Y is an alkylene chain containing 1 or 2 carbon atoms optionally substituted by one or more alkyl groups containing 1 to 3 carbon atoms;
Z is an alkylene chain containing 2 to 5 carbon atoms optionally substituted by one or more alkyl groups containing 1 to 3 carbon atoms;
R is phenyl optionally substituted by one or more halo substituents or R is naphthyl; and
$R_1$ and $R_2$ which are the same or different, are H, a straight or branched chain alkyl group containing 1 to 4 carbon atoms, an arylalkyl group in which the alkyl group contains 1 to 3 carbon atoms, provided that when $R_1$ is benzyl, $R_2$ is H or methyl;
to the mammal in need thereof.

16. A method according to claim 15, wherein the addictive substance is cocaine, amphetamine, nicotine, opiates, tobacco, alcohol or ecstasy.

17. A method according to claim 15, wherein m is 0, 1 or 2 and n is 3 or 4.

18. A method according to claim 15, wherein X is carbonyl or the group of formula II in which $R_5$ is H.

19. A method according to claim 15, wherein Y is methylene.

20. A method according to claim 15, wherein Z is an alkylene chain containing 2 to 4 carbon atoms optionally substituted by one or more alkyl groups containing 1 to 3 carbon atoms.

21. A method according to claim 15, wherein Z is an alkylene chain containing 2 to 4 carbon atoms optionally substituted by one or more methyl groups.

22. A method according to claim 15, wherein R is phenyl substituted by one or two chloro substituents or R is naphthyl.

23. A method according to claim 15, wherein R is 3-chlorophenyl; 3,4-dichlorophenyl; or 2-naphthyl.

24. A method according to claim 15, wherein $R_1$ is an alkyl group containing 1 to 3 carbon atoms or is benzyl, and $R_2$ is an alkyl group containing 1 to 3 carbon atoms.

25. A method according to claim 15, wherein $R_1$ and $R_2$ are both methyl or ethyl or $R_1$ is benzyl and $R_2$ is methyl.

26. A method of reducing cravings to an addictive substance in a mammal comprising administering an effective amount of a compound of formula III

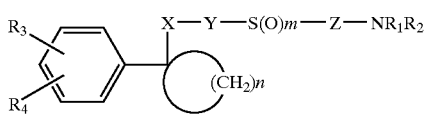

and pharmaceutically acceptable salts thereof wherein:
m is 0, 1 or 2;
n is 2, 3, 4 or 5;
X is carbonyl or a group of formula II

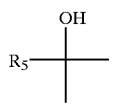

and wherein $R_5$ is H or an alkyl group containing 1 to 4 carbon atoms;
Y is an alkylene chain containing 1 or 2 carbon atoms optionally substituted by one or more alkyl groups containing 1 to 3 carbon atoms;
Z is an alkylene chain containing 2 to 5 carbon atoms optionally substituted by one or more alkyl groups containing 1 to 3 carbon atoms;
$R_1$ and $R_2$, which are the same or different, are H, a straight or branched chain alkyl group containing 1 to 4 carbon atoms, an arylalkyl group in which the alkyl group contains 1 to 3 carbon atoms, provided that when $R_1$ is benzyl, $R_2$ is H or methyl; and
$R_3$ is halo, and $R_4$ is H or halo, or $R_3$ and $R_4$ together with the carbon atoms to which they are attached form a fused benzene ring;
to the mammal in need thereof.

27. A method according to claim 26, wherein $R_3$ is chloro and $R_4$ is H, $R_3$ and $R_4$ being both chloro or $R_3$ and $R_4$ together with the carbon atoms to which they are attached forming a fused benzene ring.

28. A method according to claim 26, wherein $R_3$ is chloro situated in the 3-substitution position on the phenyl ring and $R_4$ is H, $R_3$ and $R_4$ being both chloro and situated in the 3- and 4-substitution positions on the phenyl ring respectively, or $R_3$ and $R_4$ together with the phenyl ring to which they are attached forming a 2-naphthyl group.

29. A method according to claim 15, wherein the compound of formula I is selected from the group consisting of:
1-[1-(3,4-dichlorophenyl)cyclobutyl]-2-[2-(dimethylamino)ethylthio]ethanone;
1-[1-(3,4-dichlorophenyl)cyclobutyl]-2-[2-(dimethylamino)ethylsulphinyl]ethanone;
1-[1-(3,4-dichlorophenyl)cyclobutyl]-2-[2-(dimethylamino)ethylsulphonyl]ethanone;
1-[1-(3,4-dichlorophenyl)cyclobutyl]-2-[2-(diethylamino)ethylthio]ethanone;
2-[2-(N-benzyl-N-methylamino)ethylthio]-1-[1-(3,4-dichlorophenyl)cyclobutyl]ethanone;
1-[1-(3,4-dichlorophenyl)cyclobutyl]-2-[2-(dimethylamino)ethylthio]ethanol;
1-[1-(3,4-dichlorophenyl)cyclobutyl]-2-[3-(dimethylamino)propylthio]ethanone;
1-[1-(3,4-dichlorophenyl)cyclobutyl]-2-[3-(dimethylamino)propylsulphonyl]ethanone;
1-[1-(3,4-dichlorophenyl)cyclobutyl]-2-[3-(dimethylamino)propylthio]ethanol;
1-[1-(3,4-dichlorophenyl)cyclobutyl]-2-[3-(dimethylamino)-2 methylpropylthio]-ethanone;
2-[2-(dimethylamino)ethylthio]-1-(1-(2-naphthyl)cyclobutyl]ethanone;
1-[1-(3-chlorophenyl)cyclobutyl]-2-[3-(dimethylamino)propylthio]ethanone;
1-[1-(3,4-dichlorophenyl)cyclobutyl]-2-[4-(dimethylamino)butylthio]ethanone;
1-[1-(3,4-dichlorophenyl)cyclobutyl]-2-[3-(dipropylamino)propylthio]ethanone;
1-[13,4-dichlorophenyl)cyclobutyl]-2-[3-(dimethylamino)2-methylpropylthio]ethanol;
1-[1-(3,4-dichlorophenyl)cyclopentyl]-2-[3-(dimethylamino)propylthio]ethanone; and
pharmaceutically acceptable salts thereof in the form of individual enantiomers, racemates, or other mixtures of enantiomers.

30. A method according to claim 17, wherein the addictive substance is cocaine, amphetamine, nicotine, opiates, tobacco, alcohol or ecstasy.

31. A method according to claim 18, wherein the addictive substance is cocaine, amphetamine, nicotine, opiates, tobacco, alcohol or ecstasy.

32. A method according to claim 19, wherein the addictive substance is cocaine, amphetamine, nicotine, opiates, tobacco, alcohol or ecstasy.

33. A method according to claim 20, wherein the addictive substance is cocaine, amphetamine, nicotine, opiates, tobacco, alcohol or ecstasy.

34. A method according to claim 21, wherein the addictive substance is cocaine, amphetamine, nicotine, opiates, tobacco, alcohol or ecstasy.

35. A method according to claim 22, wherein the addictive substance is cocaine, amphetamine, nicotine, opiates, tobacco, alcohol or ecstasy.

36. A method according to claim 23, wherein the addictive substance is cocaine, amphetamine, nicotine, opiates, tobacco, alcohol or ecstasy.

37. A method according to claim 24, wherein the addictive substance is cocaine, amphetamine, nicotine, opiates, tobacco, alcohol or ecstasy.

38. A method according to claim 25, wherein the addictive substance is cocaine, amphetamine, nicotine, opiates, tobacco, alcohol or ecstasy.

39. A method according to claim 26, wherein the addictive substance is cocaine, amphetamine, nicotine, opiates, tobacco, alcohol or ecstasy.

40. A method according to claim 27, wherein the addictive substance is cocaine, amphetamine, nicotine, opiates, tobacco, alcohol or ecstasy.

41. A method according to claim 28, wherein the addictive substance is cocaine, amphetamine, nicotine, opiates, tobacco, alcohol or ecstasy.

42. A method according to claim 29, wherein the addictive substance is cocaine, amphetamine, nicotine, opiates, tobacco, alcohol or ecstasy.

43. A method of reducing cravings to food in a mammal comprising administering an effective amount of a compound of formula I

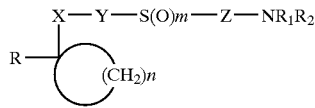

and pharmaceutically acceptable salts thereof in which
m is 0,1 or 2;
n is 2,3,4 or 5;
X is carbonyl or a group of formula II

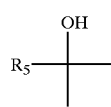

in which $R_5$ is H or an alkyl group containing 1 to 4 carbon atoms;
  Y is an alkylene chain containing 1 2 carbon atoms optionally substituted by one or more alkyl groups containing 1 to 3 carbon atoms;
  Z is an alkylene chain containing 2 to 5 carbon atoms optionally substituted by one or more alkyl groups containing 1 to 3 carbon atoms;
  R is phenyl optionally substituted by one or more halo substituents or R is naphthyl; and
  $R_1$ and $R_2$ which are the same or different, are H, a straight or branched chain alkyl group containing 1 to 4 carbon atoms, an arylalkyl group in which the alkyl group contains 1 to 3 carbon atoms, provided that when $R_1$ is benzyl, $R_2$ is H or methyl; to the mammal in need thereof, wherein the method is not used to treat obesity.

44. A method according to claim 43, wherein m is 0,1 or 2 and n is 3 or 4.

45. A method according to claim 43, wherein X is carbonyl or the group of formula II in which $R_5$ is H.

46. A method according to claim 43, wherein Y is methylene.

47. A method according to claim 43, wherein Z is alkylene chain containing 2 to 4 carbon atoms optionally substituted by one one or more alkyl groups containing 1 to 3 carbon atoms.

48. A method according to claim 43, wherein Z is an alkylene chain containing 2 to 4 carbon atoms optionally substituted by one or more methyl groups.

49. A method according to claim 43, wherein R is phenyl substituted by one or two chloro substituents or R is naphthyl.

50. A method according to claim 43, wherein R is 3-chlorophenyl; 3,4-dichlorophenyl; or 2-naphthyl.

51. A method according to claim 43, wherein $R_1$ is an alkyl group containing 1 to 3 carbon atoms or is benzyl, and $R_2$ is an alkyl group containing 1 to 3 carbon atoms.

52. A method according to claim 43, wherein $R_1$ and $R_2$ are both methyl or ethyl or $R_1$ is benzyl and $R_2$ is methyl.

53. A method according to claim 43, wherein the compound of formula I is selected from the group consisting of:
  1-[1-(3,4-dichlorophenyl) cyclobutyl]-2-[2-(dimethylamino) ethylthio] ethanone;
  1-[1-(3,4-dichlorophenyl) cyclobutyl]-2-[2-(dimethylamino) ethylsulphinyl]ethanone;
  1-[1-(3,4-dichlorophenyl) cyclobutyl]-2-[2-(dimethylamino) ethylsulphonyl]ethanone;
  2-[2-(N-benzyl-N-methylamino) ethylthio]-1-[1-(3,4-dichlorophenyl)cyclobutyl]- ethanone;
  1-[1-(3,4-dichlorophenyl) cyclobutyl]-2-[2-(dimethylamino) ethylthio] ethanol;
  1-[1-(3,4-dichlorophenyl) cyclobutyl]-2-[3-(dimethylamino) propylthio] ethanone;
  1-[1-(3,4-dichlorophenyl) cyclobutyl]-2-[3-(dimethylamino) propylsulphonyl] ethanone;
  1-[1-(3,4-dichlorophenyl) cyclobutyl]-2-[3-(dimethylamino) propylthio] ethanol;
  1-[1-(3,4-dichlorophenyl) cyclobutyl]-2-[3-(dimethylamino)-2-methylpropylthio]-ethanone;
  2-[2-(dimethylamino) ehtylthio]-1-(1-(2-naphthyl) cyclobutyl] ethanone;
  1-[1-(3-chlorophenyl) cyclobutyl]-2-[3- (dimethylamino) propylthio] ethanone;
  1-[1-(3,4-dichlorophenyl) cyclobutyl]-2-[4- (dimethylamino) butylthio] ethanone;
  1-[1-(3,4-dichlorophenyl) cyclobutyl]-2-[3- (dipropylamino) propylthio] ethanone;
  1-[1-(3,4-dichlorophenyl) cyclobutyl]-2-[3-(dimethylamino)-2-methylpropylthio] ethanol;
  1-[1-(3,4-dichlorophenyl) cyclobutyl]-2-[3-(dimethylamino) propylthio] ethanone; and
  pharmaceutically acceptable salts thereof in the form of individual enantiomers, racemates, or other mixtures of enantiomers.

54. A method of reducing cravings to food in a mammal comprising administering an effective amount of a compound of formula III

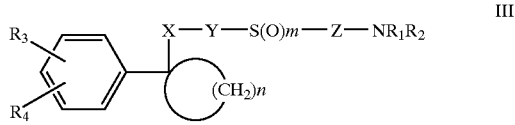

and pharmaceutically acceptable salts thereof wherein:
  m is 0,1 or 2;
  n is 2,3,4 or 5;

X is carbonyl or a group of formula II

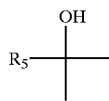

and wherein $R_5$ is H or an alkyl group containing 1 to 4 carbon atoms;

Y is an alkylene chain containing 1 or 2 carbon atoms optionally substituted by one or more alkyl groups containing 1 to 3 carbon atoms;

Z is an alkylene chain containing 2 to 5 carbon atoms optionally substituted by one or more alkyl groups containing 1 to 3 carbon atoms;

$R_1$ and $R_2$, which are the same or different, are H, a straight or branched chain alkyl group containing 1 4 carbon atoms, and arylalkyl group in which the alkyl group contains 1 to 3 atoms, provided that when $R_1$ is benzyl, $R_2$ is H or methyl; and $R_3$ $_{is\ halo,\ and\ R4}$ is H or halo, or $R_3$ and $R_4$ together with the carbon atoms to which they are attached form a fused benzene ring; to the mammal in need thereof, wherein the method is not used to treat obesity.

55. A method according to claim 54, wherein $R_3$ is chloro and $R_4$ is H, $R_3$ and $R_4$ being both chloro or $R_3$ and $R_4$ together with the carbon atoms to which they are attached forming a fused benzene ring.

56. A method according to claim 54, wherein $R_3$ is chloro situated in the 3-substitution position on the phenyl ring an $R_4$ is H, $R_3$ and $R_4$ being both chloro and situated in the 3-and 4-substitution positions on the phenyl ring respectively, or $R_3$ and $R_4$ together with the phenyl ring to which they are attached forming a 2-naphthyl group.

\* \* \* \* \*